(12) United States Patent
Harish et al.

(10) Patent No.: US 8,597,199 B2
(45) Date of Patent: Dec. 3, 2013

(54) REDUCED-PAIN ALLERGY SKIN TEST DEVICE

(76) Inventors: Ziv Harish, Tenafly, NJ (US); Isaac Rubinstein, Haworth, NJ (US); Ehud Arbit, Englewood, NJ (US); Russ Weinzimmer, Milford, NH (US)

( * ) Notice: Subject to any disclaimer, the term of this patent is extended or adjusted under 35 U.S.C. 154(b) by 237 days.

(21) Appl. No.: 12/902,030

(22) Filed: Oct. 11, 2010

(65) Prior Publication Data
US 2012/0089048 A1 Apr. 12, 2012

(51) Int. Cl.
*A61B 5/00* (2006.01)
(52) U.S. Cl.
USPC .......................................................... 600/556
(58) Field of Classification Search
USPC ..................... 600/556; 604/46, 47
See application file for complete search history.

(56) References Cited

U.S. PATENT DOCUMENTS

| | | |
|---|---|---|
| 2,841,138 A | 7/1958 | Laub |
| 3,556,080 A | 1/1971 | Hein |
| 3,688,764 A | 9/1972 | Reed |
| 4,109,655 A | 8/1978 | Chacornac |
| 4,222,392 A | 9/1980 | Brennan |
| 4,607,632 A | 8/1986 | Brennan et al. |
| 5,076,282 A | 12/1991 | Fishman et al. |
| 5,749,836 A | 5/1998 | Hsiao |
| 5,820,562 A | 10/1998 | Hsiao |
| 5,964,729 A | 10/1999 | Choi et al. |
| 6,611,707 B1 | 8/2003 | Prausnitz et al. |
| 6,629,949 B1 | 10/2003 | Douglas |
| 6,743,211 B1 | 6/2004 | Prausnitz et al. |
| 7,226,439 B2 | 6/2007 | Prausnitz et al. |
| 7,422,567 B2 | 9/2008 | Lastovich et al. |
| 2006/0178615 A1 | 8/2006 | Ronborg et al. |
| 2008/0086159 A1 | 4/2008 | Zweifler |
| 2008/0294183 A1 | 11/2008 | O |

FOREIGN PATENT DOCUMENTS

| | | |
|---|---|---|
| CN | 2129604 Y | 4/1993 |
| CN | 2750778 Y | 1/2006 |
| KR | 0792640 B1 | 1/2008 |
| WO | 2008007906 A1 | 1/2008 |

OTHER PUBLICATIONS

Website: http://www.diabeticmctoday.com/HtmlPages/DMC0706/dmc0706neurojacobs.pdf Downloaded Jun. 28, 2010 Cutaneous Pinprick Sensibility as a Screening Device article.
Website: http://www.biomedcentral.com/1472-6882/7/31 Downloaded Jun. 28, 2010 Double-blind placebo and matched needle article.

*Primary Examiner* — Brian Szmal
(74) *Attorney, Agent, or Firm* — Russ Weinzimmer & Associates P.C.

(57) ABSTRACT

An allergy skin test device is disclosed that causes less pain than commonly used devices that include multi-point sharp puncture heads. The allergy skin test device incorporates multiple dull pressure heads distributed amongst the sharp multi-point sharp puncture heads, each dull pressure head activating a neurological pain gate that reduces pain sensation typically caused by the neighboring multi-point head when it engages the skin.

16 Claims, 7 Drawing Sheets

REDUCED-PAIN ALLERGY SKIN TEST DEVICE

FIELD OF THE INVENTION

This invention relates generally to allergy skin test devices, and particularly to allergy skin test devices having sharp points.

BACKGROUND OF THE INVENTION

Allergy skin testing is based on introducing allergens into the skin. There are numerous known devices for introducing allergens using a plurality of closely spaced sharp probes. The test often causes pain, resulting in patient reluctance to complete the test, and frequently interferes with the otherwise calm nature of a medical office.

As a result of the felt pain, patients will sometimes react with loud expressions of pain. Children will actually sometimes cry and scream. These audible reactions can negatively affect the patients that follow, creating further difficulties with patient compliance.

SUMMARY OF THE INVENTION

As recognized by the invention, introduction of dull pressure in the proximity of a sharp stimulus to the skin will tend to block perception of the normally resulting sharp pain sensation. This is an application of what is sometimes referred to as "neurological pain gate theory". The device of the invention advantageously exploits this effect for the first time in the field of allergy testing by first applying dull pressure by means of dull pressure heads regularly interspersed among a regular array of sharp puncture heads. The dull pressure heads are slightly longer than the sharp ones, and consequently, they touch the skin before the sharp heads as the sharp heads are pressed into the skin.

Each dull head is supported on a flexible member, and when the allergy skin test device of the invention is pressed into the skin, the flexible member is urged into a flexed condition so as to apply pressure of a magnitude sufficient to activate the "pain gate" effect in the pain receptors that would otherwise be activated by the sharp puncture head. The dull heads are flexible enough to apply sufficient pressure, while not interfering with the sharp puncture heads' ability to puncture the skin and introduce the allergens. In clinical testing of the device, subjects reported significantly less pain when compared to devices that do not include the dull heads.

A first general aspect of the invention is an allergy skin test device, where the device includes a plurality of sharp puncture heads, and a plurality dull pressure heads, the plurality of dull pressure heads being interspersed among the plurality of sharp puncture heads, at least one dull pressure head being cooperative with a sharp puncture head so as to promote a pain gate effect that reduces pain sensation caused by the sharp puncture head.

In preferred embodiments, the plurality of sharp puncture heads is arranged as a regular array of sharp puncture heads. In further preferred embodiments, the regular array is one of: a square array, a rectangular array, a linear array, a polygonal array, an oval array, a circular array, an ellipsoidal array, a radially symmetric array.

In other preferred embodiments, there is a dull pressure head for each sharp puncture head.

In yet other preferred embodiments, the at least one dull pressure head is cooperative with the sharp puncture head by being positioned so as to be able to contact skin of a patient before the cooperative sharp puncture head contacts the skin of the patient when the device is used.

In still other preferred embodiments, both the plurality of sharp puncture heads, and the plurality dull pressure heads, extend from a gripping element used to apply the allergy skin test device to the skin of the patient. In further preferred embodiments, the gripping element is one of: a linearly extended member, a central hub member, a curved extended member, a round member, an oval member, an ellipsoidal member.

In preferred embodiments, each dull pressure head is supported by a flexible arm that is sufficiently resistant to bending so as to apply pressure via the dull pressure head sufficient to promote a pain gate effect that reduces pain sensation caused by the sharp puncture head when it contacts the skin of the patient after the dull pressure head contacts the skin of the patient when the device is used.

In other preferred embodiments, each dull pressure head is supported by a compressible column that is sufficiently resistant to being compressed so as to apply pressure via the dull pressure head sufficient to promote a pain gate effect that reduces pain sensation caused by the sharp puncture head when it contacts the skin of the patient after the dull pressure head contacts the skin of the patient when the device is used.

Another general aspect of the invention is an allergy skin test device having a regular array of sharp puncture heads; a corresponding regular array of dull pressure heads, each of the sharp puncture heads being cooperative with a dull pressure head so as to contact the skin before the corresponding sharp puncture head; and a gripping element used to apply the allergy skin test device to the skin of the patient, both the regular array of sharp puncture heads, and the corresponding regular array of dull pressure heads, extending from the gripping element.

In preferred embodiments, each sharp puncture head is supported by a first flexible arm cooperative with the gripping element, each dull pressure head is supported by a second flexible arm cooperative with the gripping element, each second flexible arm is in nearest neighbor relationship with the first flexible arm, and the first flexible arm is of a different length than the second flexible arm.

In other preferred embodiments, the second flexible arm is longer than the first flexible arm.

In still other preferred embodiments, the first flexible arm is longer than the second flexible arm.

In yet other preferred embodiments, the second flexible arm is less flexible than the first flexible arm.

In still yet other preferred embodiments, each dull pressure head rises higher than a nearest sharp puncture head such that when the allergy skin test is used at an angle within a range of working angles, each dull pressure head contacts skin before the nearest sharp puncture head.

In other preferred embodiments, each sharp puncture head is supported by a first compressible column, the first compressible column being supported by the gripping element, each dull pressure head is supported by a second compressible column that is in nearest neighbor relationship with the first compressible column, the second compressible column being supported by the gripping element, and the first compressible column is shorter than the second compressible column.

Another general aspect of the invention is an allergy skin test device including a sharp puncture head; a plurality of dull pressure heads, each dull pressure head being cooperative with the sharp puncture head so as to resiliently contact the skin before the sharp puncture head; and a gripping element for gripping the allergy skin test device, for supporting the sharp puncture head and the plurality of dull pressure heads, and for applying pressure to skin of a patient via the sharp puncture head and the plurality of dull pressure heads.

In preferred embodiments, each of the dull pressure heads is supported by a flexible arm that can apply sufficient pressure to provide a pain gate effect when contacting skin of a patient, without interfering with puncturing of skin by the sharp puncture head when used to introduce allergens into the skin.

In other preferred embodiments, each of the dull pressure heads is supported by a compressible column that applies sufficient pressure to provide a pain gate effect when contacting skin of a patient, without interfering with puncturing of skin by the sharp puncture head when used to introduce allergens into the skin.

Another general aspect of the invention is an allergy skin test device that includes a first applicator supporting a plurality of dull pressure heads, and having a plurality of holes interspersed among the plurality of dull pressure heads; and a second applicator, cooperative with the first applicator, the second applicator supporting a plurality of sharp puncture heads, the plurality of sharp puncture heads being sized and positioned so as to be able to simultaneously move through the plurality of holes, the plurality of dull pressure heads of the second applicator being interspersed among a plurality of holes sized so as to allow passage therethrough of the plurality of sharp puncture heads, at least one dull pressure head being cooperative with a sharp puncture head so as to promote a pain gate effect that reduces pain sensation caused by the sharp puncture head.

BRIEF DESCRIPTION OF THE DRAWING

The invention will be more fully understood from the following detailed description, in conjunction with the following figures, wherein.

DETAILED DESCRIPTION

Figure 1:
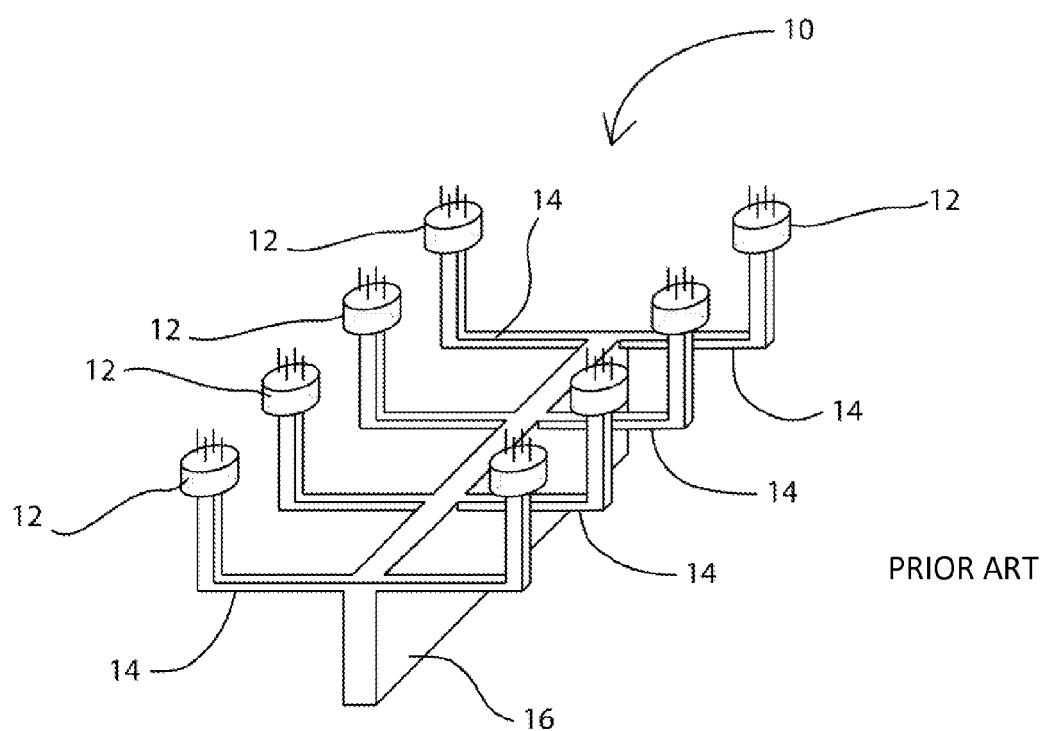
FIG. 1 is a perspective view of an allergy skin test device of the prior art.

With reference to FIG. 1, a known allergy skin test device 10 is shown. The device 10 has a plurality of sharp puncture heads 12, each sharp puncture head 12 being supported on a support arm 14. Each support arm 14 is attached or integral with a gripping element 16 that is used to hold the allergy skin test device 10 when applying the device to the skin of a patient for allergy testing. This is a common allergy skin testing scenario, with the attendant pain and distress for a significant number of patients, because the sharp puncture heads each have a plurality of sharp probes that must penetrate into the skin. Such penetration causes pain and occasionally even some bleeding. Even when the pain and the bleeding are minor and temporary, they still present a problem for the medical personnel who must administer such tests. The pain is more of an issue than the minor and sporadic bleeding, since the pain more often elicits loud patient reactions, particularly among the young patients, and often interferes with patient's willingness to return for further or follow up testing.

Figure 2:
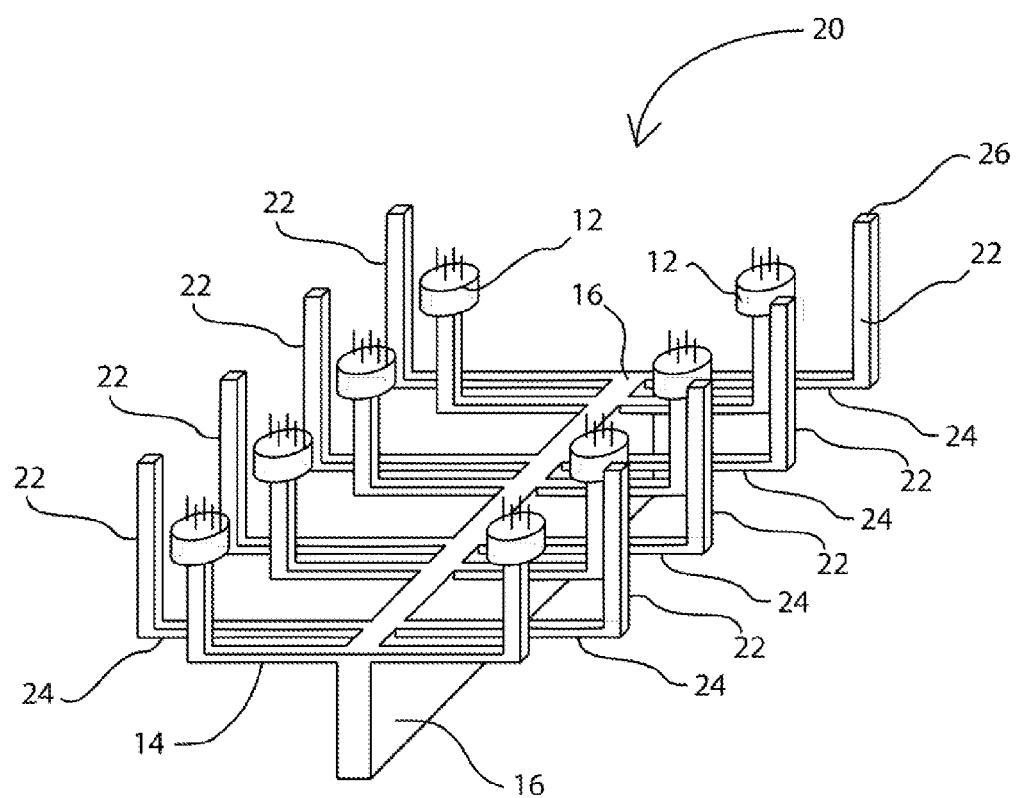
FIG. 2 is a perspective view of an allergy skin test device of the invention having two linear arrays of sharp puncture heads and two corresponding linear arrays of dull pressure heads.

With reference to FIG. 2, an allergy skin test device 20 of the invention is shown, having all the elements of the known device, as well as a plurality of dull heads 22 supported on flexible arms 24. In this embodiment, the flexible arms 24 are longer than the corresponding arms 14 that support each corresponding sharp puncture head 12. However, it's also possible that a dull head can be supported on a flexible arm that is shorter than the flexible arm that supports the corresponding sharp puncture head.

In either case, the dull head 22 is taller than the sharp puncture head 12, and consequently, when the allergy skin test device of the invention is applied to the skin of a patient, each dull head 22 will press against the skin BEFORE the corresponding nearby sharp puncture head 12. This results in pressure applied to the skin nearby where the sharp punctures occur, and this pressure effects a neural mechanism that results in substantially "gating" pain sensations caused by the penetration of the sharp elements of the sharp puncture head 12 into the skin.

In our testing, we discovered that pain in the arm was effectively blocked when the dull head is within ¼ of an inch in lateral distance from the sharp head.

As to the height difference between the sharp head and the dull head, it is important that the dull head is higher so as to apply perceivable pressure to the arm before the sharp head first touches the arm. In our tests, 11b of force applied over the surface area of a dull head of 1/16" in diameter was not enough. 2-3 lb applied over the surface area (e.g., 1/16 sq inch) of the same dull head caused a desirable pain gating effect. For skin test devices made of standard material, and where the arms that support the dull heads are made from this standard material, the height of each dull head can be about $1/8^{th}$ of an inch higher than the highest point of a respective sharp head. In general, the restoring force as provided by the supporting arms (or supporting compressible columns) must provide the 2-3 lbs of force over the dull head surface area needed to cause the desired pain-gating effect.

An important aspect of the height difference is that the dull heads contact the skin before the sharp head(s), regardless of which attack angle is used, wherein the attack angle falls within a range of working angles. Alternatively, one can define the range of working angles as the range of angles that ensure that the dull heads contact the skin with enough pressure to ensure a pain-gating effect. For example, such a range of working angles can be all angles within about 30 degrees of a normal vector that is perpendicular to the skin surface to be tested.

The inclusion a flexible arm or compressible column (as opposed to a substantially inflexible arm or substantially non-compressible column) is to ensure that while the dull head applies sufficient pressure, it does not preclude the sharp head from sufficiently penetrating the skin.

Figure 3:
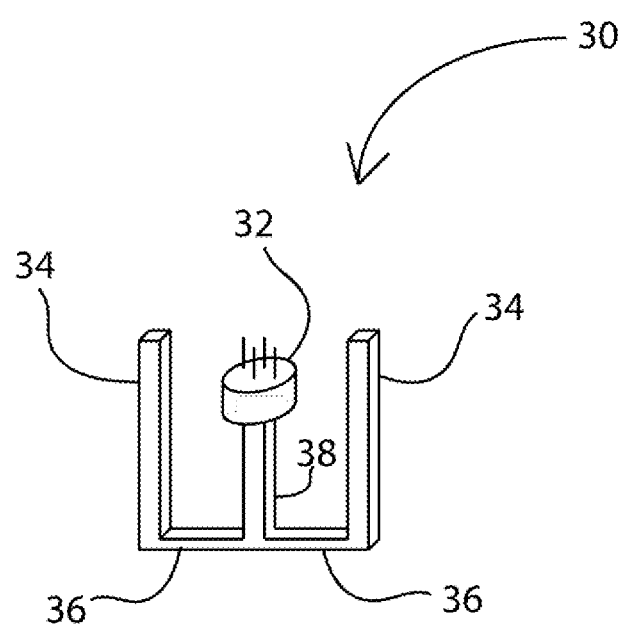
FIG. 3 is a perspective view of an allergy skin test device having a single sharp puncture head, plus a plurality of dull heads on a flexible arm in the proximity of the sharp head.

FIG. 3 shows another preferred embodiment 30 having a single sharp puncture head 32, plus one or more dull heads 34 (e.g., two, as shown), each on a flexible arm 36 in the proximity of the sharp head 32. The flexible arms 36 can be grasped near and along with the supporting member 38 to apply the single sharp head 32 to the skin of a person to be tested for an allergen.

Figure 4:
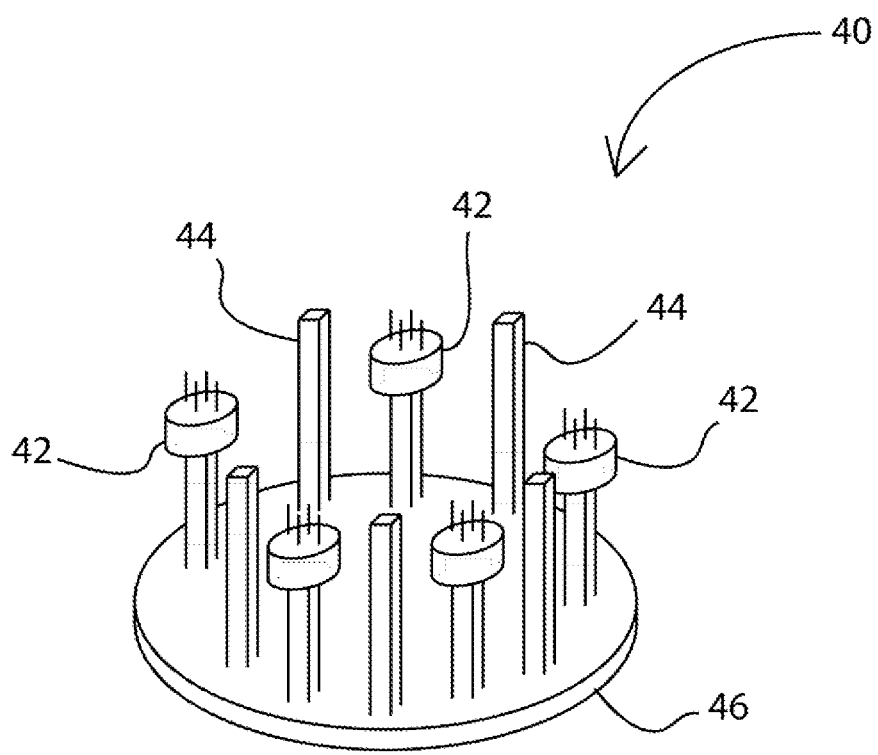
FIG. 4 is a perspective view of an allergy skin test device having a circular array of sharp puncture heads, also having a corresponding circular array of dull heads, each dull head being in proximity to each sharp puncture head.

FIG. 4 shows another preferred embodiment 40 having a circular array of sharp puncture heads, (e.g., five sharp puncture heads) 42 also having a corresponding circular array of dull heads 44, each dull head 44 being in proximity to each respective sharp puncture head 42. All of the sharp puncture heads 42 and the respective dull pressure heads 44 are supported by a support element 46, which can include a grasping portion (not shown) that is used to grasp and control the entire embodiment 40 so as to facilitate application of the sharp puncture heads 42 and the dull pressure heads 44 of the embodiment 40 to the skin.

Figure 5:
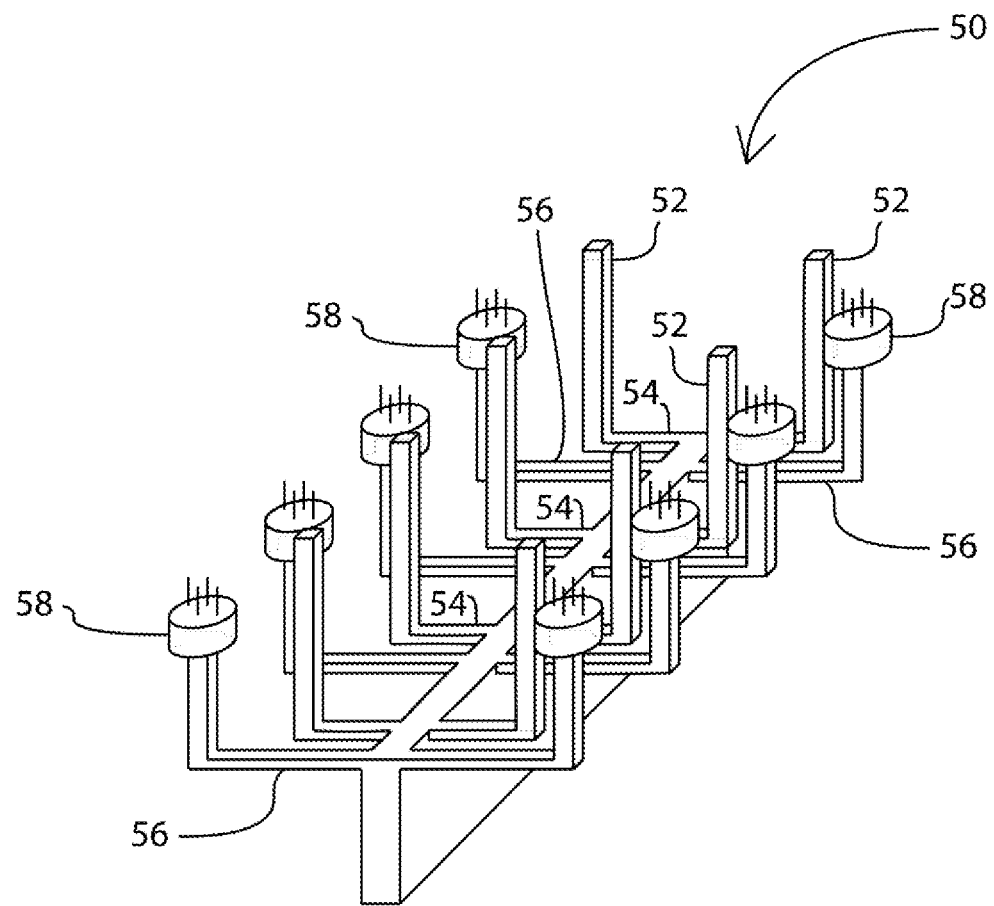
FIG. 5 is a perspective view of an allergy skin test device of the invention having dull heads that are supported by arms that are shorter than the arms that support the sharp puncture heads.

FIG. 5 shows another preferred embodiment 50 where the dull heads 52 are supported on arms 54 shorter than the arms 56 that support the sharp puncture heads 58. The key is that each dull head applies 2-3 lb of force over the dull head surface area (e.g., 1/16 sq inch) so as to provide the desired pain-gating effect.

Figures 6A, 6B:
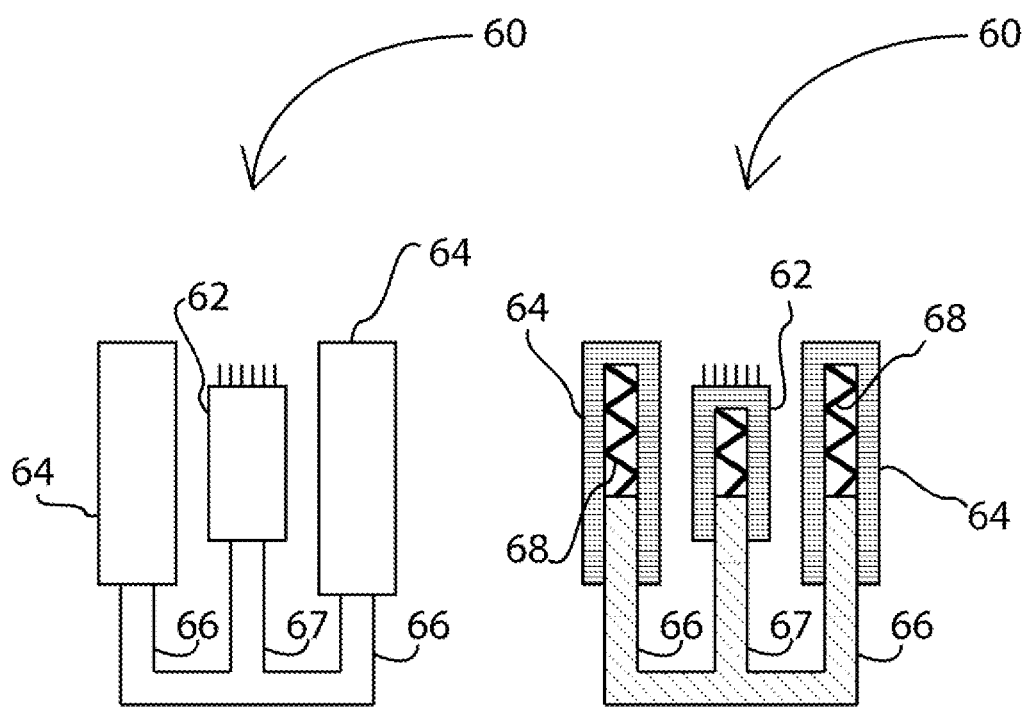
FIGS. 6A and 6B are perspective views of an embodiment wherein both the sharp puncture heads and the dull pressure heads are each supported by compressible columns.

FIGS. 6A and 6B show external and cutaway views, respectively, of an embodiment 60 wherein both the sharp puncture heads 62 and the dull pressure heads 64 are each supported by compressible columns 66, 67. Note that each compressible column 66 includes a compressible element 68 that stores compression potential energy when the compressible columns 66 are pressed towards the surface of skin to be tested. In this embodiment, compressible element 68 of each dull pressure head 64 applies 2-3 lb of force over the dull head surface area (e.g., 1/16 sq inch) so as to provide the desired pain-gating effect. Also, each sharp head 62 is supported on a compressible column 67 that provides sufficient pressure to enable the sharp head probes to penetrate the skin effectively.

Figure 7:
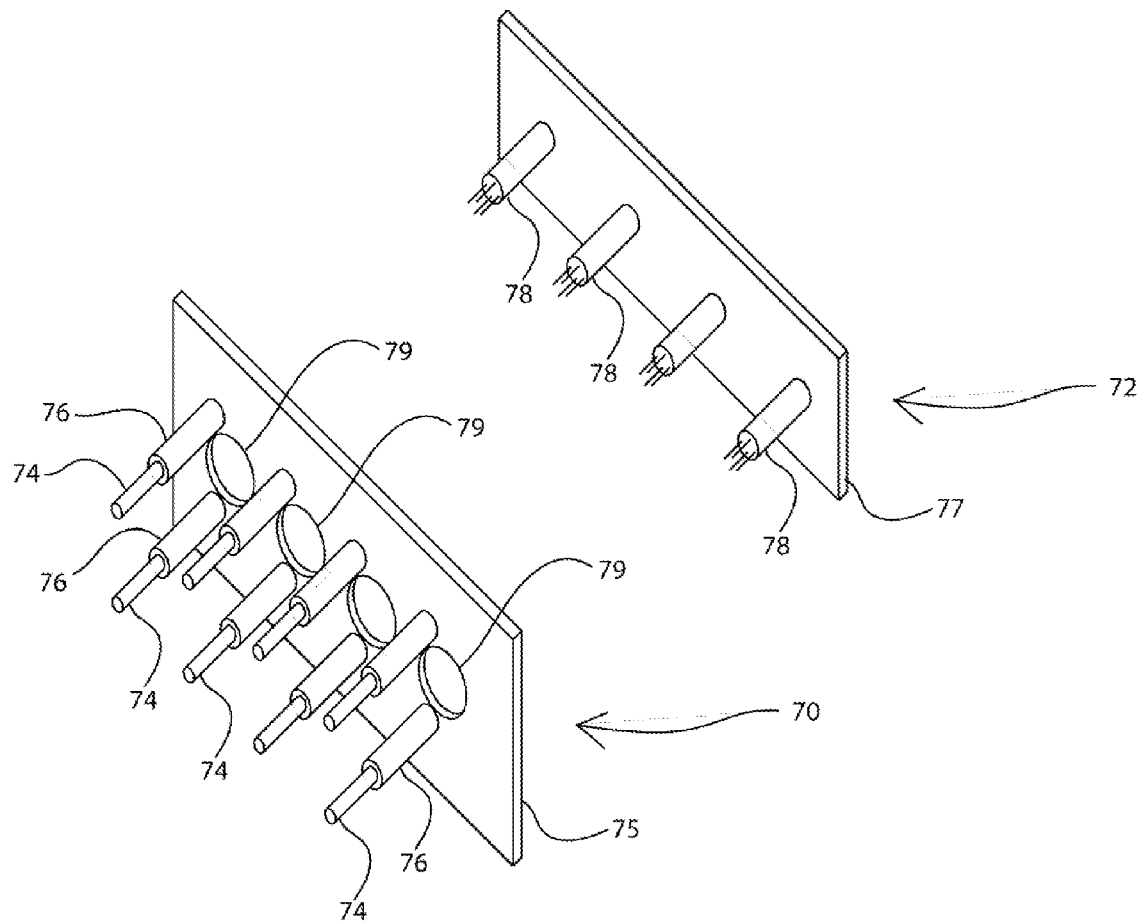
FIG. 7 is a perspective view of a two-part embodiment, having a dull head portion and a sharp puncture head portion

FIG. 7 shows a two-part embodiment, having a dull head portion 70 and a sharp puncture head portion 72. The dull head portion 70 includes a plurality of dull pressure heads 74 supported on a support element 75, which supports a plurality of compressible columns 76 for each dull pressure head 74.

The sharp puncture head portion 72 includes support element 77 that supports a plurality of sharp puncture heads 78, each puncture head being supported on either a compressible or non-compressible column.

To use this embodiment, the dull head portion 70 is first pressed via support element 75 against the skin of a person to be tested. The sharp puncture head portion 72 can then be grasped via the support element 77.

While dull pressure is thereby applied using the dull head portion 70, the sharp puncture head portion 72 is pressed via support element 77 against the skin such that each sharp puncture head 78 contacts the skin via a corresponding hole 79.

Other modifications and implementations will occur to those skilled in the art without departing from the spirit and the scope of the invention as claimed. Accordingly, the above description is not intended to limit the invention, except as indicated in the following claims.

What is claimed is:

1. An allergy skin test device, the device comprising:
a plurality of sharp puncture heads; and
a plurality dull pressure heads,
the plurality of dull pressure heads being interspersed among the plurality of sharp puncture heads,
at least one dull pressure head being cooperative with a sharp puncture head so as to promote a pain gate effect that reduces pain sensation caused by the sharp puncture head.

2. The allergy skin test device of claim 1, wherein the plurality of sharp puncture heads is arranged as a regular array of sharp puncture heads.

3. The allergy skin testing device of claim 2, wherein the regular array is one of:
a square array, a rectangular array, a linear array, a polygonal array, an oval array, a circular array, an ellipsoidal array, a radially symmetric array.

4. The allergy skin test device of claim 1, wherein there is a dull pressure head for each sharp puncture head.

5. The allergy skin test device of claim 1, wherein the at least one dull pressure head and the sharp puncture head with which it cooperates are physically positioned relative to one another so that when the skin test device is applied with pressure to the skin of a patient, the at least one dull pressure head is adapted to contact the skin before the cooperative sharp puncture head.

6. The allergy skin test device of claim 1, further comprising:
a gripping element, and
wherein both the plurality of sharp puncture heads, and the plurality dull pressure heads, are supported by arms coupled to and extending from the gripping element.

7. The allergy skin test device of claim 6, wherein the gripping element is one of:
a linearly extended member, a central hub member, a curved extended member, a round member, an oval member, an ellipsoidal member.

8. The allergy skin test device of claim 1, wherein:
each dull pressure head is supported by a flexible arm, the flexible arm extending the dull pressure head supported thereon beyond any sharp puncture heads adjacent thereto so that when the skin test device is applied with pressure to the skin of a patient:
each dull pressure head is thereby configured to contact the skin before the sharp puncture heads adjacent thereto.

9. An allergy skin test device, the device comprising:
a regular array of sharp puncture heads;
a corresponding regular array of dull pressure heads, each of the sharp puncture heads being cooperative with a dull pressure head so as to contact the skin before the corresponding sharp puncture head; and
a gripping element used to apply the allergy skin test device to the skin of the patient, both the regular array of sharp puncture heads, and the corresponding regular array of dull pressure heads, extending from the gripping element.

10. The allergy skin test device of claim 9, wherein
each sharp puncture head is supported by a first flexible arm cooperative with the gripping element,
each dull pressure head is supported by a second flexible arm cooperative with the gripping element,
each second flexible arm is in nearest neighbor relationship with the first flexible arm, and
the first flexible arm is of a different length than the second flexible arm.

11. The allergy skin test device of claim 9, wherein the first flexible arm is longer than the second flexible arm.

12. The allergy skin test device of claim 9, wherein the second flexible arm is less flexible than the first flexible arm.

13. The allergy skin test device of claim 9, wherein:
each dull pressure head extends further from the gripping member than a nearest sharp puncture head, and
when the allergy skin test is applied with pressure to the skin of a patient an angle within a range of working angles, each dull pressure head is adapted to contact the skin before the nearest sharp puncture head.

14. An allergy skin test device, the device comprising:
a sharp puncture head;
a plurality of dull pressure heads, each dull pressure head being cooperative with the sharp puncture head so as to resiliently contact the skin before the sharp puncture head; and
a gripping element for gripping the allergy skin test device, for supporting the sharp puncture head and the plurality of dull pressure heads, and for applying pressure to skin of a patient via the sharp puncture head and the plurality of dull pressure heads.

15. The allergy skin test device of claim 14, wherein:
each of the dull pressure heads is supported by a flexible arm, and when the skin test device is applied with pressure to introduce allergens into the skin of a patient, the flexible arm is configured to transmit the applied pressure to the skin through the dull pressure head to provide a pain gate effect, while an adjacent sharp puncture head punctures the skin.

16. An allergy skin test device, the device comprising:
a first applicator supporting a plurality of dull pressure heads, and having a plurality of holes interspersed among the plurality of dull pressure heads; and
a second applicator, configured to cooperatively couple with the first applicator, the second applicator supporting a plurality of sharp puncture heads, the plurality of sharp puncture heads being sized and positioned so as to be able to simultaneously move through the plurality of holes when the first and second applicators are cooperatively coupled,
wherein when the first and second applicators are cooperatively coupled, at least one dull pressure head is cooperative with a sharp puncture head so as to promote a pain gate effect that reduces pain sensation caused by the sharp puncture head when the skin test device is applied with pressure to skin.

* * * * *